(12) United States Patent
Toma

(10) Patent No.: US 7,745,455 B2
(45) Date of Patent: Jun. 29, 2010

(54) ZALCITABINE (DDC) BOOSTED LAMIVUDINE (3TC) COMPOSITIONS FOR ANTIRETROVIRAL THERAPY

(76) Inventor: Emil Toma, 150 Berlioz, Apt. 607, Montréal, QC (CA) H3E 1K3

(*) Notice: Subject to any disclaimer, the term of this patent is extended or adjusted under 35 U.S.C. 154(b) by 21 days.

(21) Appl. No.: 11/996,764

(22) PCT Filed: Jul. 13, 2006

(86) PCT No.: PCT/CA2006/001149
§ 371 (c)(1),
(2), (4) Date: Jan. 25, 2008

(87) PCT Pub. No.: WO2007/012177
PCT Pub. Date: Feb. 1, 2007

(65) Prior Publication Data
US 2008/0214590 A1    Sep. 4, 2008

Related U.S. Application Data

(60) Provisional application No. 60/702,608, filed on Jul. 27, 2005.

(51) Int. Cl.
A61K 31/513    (2006.01)
A61P 31/18    (2006.01)
(52) U.S. Cl. .................................. 514/274
(58) Field of Classification Search ............... None
See application file for complete search history.

(56) References Cited

U.S. PATENT DOCUMENTS 5,028,595 A * 7/1991 Soo ........................ 514/49

FOREIGN PATENT DOCUMENTS

WO    WO96/23509 A1    8/1996

OTHER PUBLICATIONS

Dutschman, G.E. et al., Metabolism of 2',3'-dideoxy-2',3'-didehydro-B-L(-)-5-Fluorocytidine and its activity in combination with clinically approved anti-human immunodeficiency virus B-D(+) nucleotide analogs in vitro, Antimicrobial Agents and Chemotherapy, 1998, 1799-1804, 42-7.
Hoggard, P.G., et al., Correlation between intracellular pharmacological activation of nucleoside analogues and HIV suppression in vitro, Antivir Chem and Chemother, 2000, 353-358, 11.
Macher, A., et al., CME contraindicated antiretroviral drug combinations, New-Jersey Med., 2003, 41-43, 100-9.
Moyle, G. et al., Finding a role for zalcitabine in HAART era, Antiretroviral Therapy, 125-137, 3, (1998).
Sweeney, K.R., et al., Renal disposition and drug interaction screening of (-)-2'-deoxy-3'-thiacytidine (3TC) in the isolated perfused rat kidney, Phar Res, 1995, 1958-1963, 12-12.
Zapor, M.J., et al., Antiretrovirals, Part II: focus on non-protease inhibitor antiretrovirals (NRTIs, NNRTIs, and fusion inhibitors, 2004, 524-535, 45.

Diallo, K., et al., Molecular Impact of the M184V Mutation in Human Immunodeficiency Virus Type 1 Reverse Transcriptase, Antimicrob. Agents Chemother, 2003, 3377-3383, 47.
Gray, N.M., et al., The intracellular phosphorylation of (-)-2'-deoxy-3'-thiacytidine (3TC) and the incorporation of 3TC 5'-monophosphate into DNA by HIV-1 reverse transcriptase and human DNA polymerase γ, Biochem Pharmacol, 1995, 1043-1051, 50-7.
Eron, J.J., et al., Treatment with Lamivudine, Zidovudine, or Both in HIV-Positive Patients with 200 to 500 CD4+ Cells per Cubic Millimeter, NEJM, 1995, 1661-1669, 333-25.

(Continued)

Primary Examiner—Brian-Yong S Kwon
Assistant Examiner—Bong-Sook Baek
(74) Attorney, Agent, or Firm—Bereskin & Parr LLP/S.E.N.C.R.L., s.r.l.

(57) ABSTRACT

Boosted cytidine analogue reverse transcriptase inhibitor antiretroviral compound is a new therapeutic anti HIV option, in combination with another drug such as a NRTI or a protease inhibitor. It's heightened and sustained antiretroviral potency is due to the increased intracellular level of 3TC triphosphate, the active form of 3TC. This effect is obtained by combining 3TC, in usual doses, with a reduced dose of ddC, in the same pharmaceutical formulation. The product could be administered twice or even once daily, which is convenient, and does not increase the pill burden for the patient. The reduced ddC dosage prevents the occurrence of ddC related side effects. Other cytidine derivatives (racemic or negative enantiomers) could have the same effects as ddC and could probably be combined with 3TC, and have the same effect. On the other hand, low dose ddC may also increase the intracellular levels of other cytidine derivatives as it does for 3TC. Boosted cytidine analogue reverse transcriptase inhibitor antiretroviral compound could also be formulated in combination with another drug such as another NRTI (e.g. abacavir) or any protease inhibitor in the same capsule or tablet. This approach offers a dual anti-HIV therapy that is as efficacious as the routine triple therapy. In this way the HIV treatment cost could be significantly reduced which is imperative for resource-poor settings. This new formulation is convenient and well tolerated with no additional toxicity than that of the combining drug (NRTI or protease inhibitor) and 3TC. Moreover, this will enable a larger number of patients to benefit from the already known 3TC effects. It will also increase the 3TC effects in those organs or HIV sanctuaries with usually reduced 3TC concentrations or activity. It could be indicated in both the initial as well as in salvage HIV therapy. It could also be used for therapy optimization or simplification. Moreover, in combination with another NRTI such as abacavir, or even alone, it could be beneficial for reducing the HIV harm in resource-poor settings.

5 Claims, 2 Drawing Sheets

OTHER PUBLICATIONS

Veal, G.J., et al., Interaction between lamivudine (3TC) and other nucleoside analogues for intracellular phosphorylation, AIDS, 1996, 546-548, 10-5.

Kewn, S., et al., Lamivudine (3TC) phosphorylation and drug interactions in vitro, Biochem Pharmacol, 1997, 589-595, 54.

Becher, F., et al., Improved method for the simultaneous determination of d4T, 3TC and ddI intracellular phosphorylated anabolites in human peripheral-blood mononuclear cells using high-performance liquid chromatography/tandem mass spectrometry, rapid commun mass spectrom, 2002, 555-565, 16-6.

UNAIDS/WHO, 2006 Report on the global AIDS epidemic. UNAIDS-Geneva, Switzerland, 2006.

Barrtlett, G. J., Guidelines for the Use of Antiretroviral Agents in HIV-1-Infected Adults and Adolescents, Apr. 7, 2005, Department of Health and Human Services (DHHS).

* cited by examiner

Phosphorylation pathway of cytidine reverse transcriptase inhibitor analogues

The abbreviations used have the following meaning:

d-cyt-k = deoxycytidine kinase dcmp-k = deoxycytidine monophosphate kinase pyr-k = pyrimidine kinase (nucleoside diphosphate kinase)

RT = reverse transcriptase.

ZALCITABINE (DDC) BOOSTED LAMIVUDINE (3TC) COMPOSITIONS FOR ANTIRETROVIRAL THERAPY

CROSS-REFERENCE TO RELATED APPLICATIONS

The present application is a 371 national entry phase of International Application No. PCT/CA2006/001149, filed on Jul. 13, 2006, and claims priority on U.S. Provisional Application No. 60/702,608 filed on Jul. 27, 2005.

BACKGROUND OF THE INVENTION (a) Field of the Invention

The present invention relates to a method for improving the antiretroviral activity of a cytidine analogue reverse transcriptase inhibitor; a boosted cytidine analogue reverse transcriptase inhibitor antiretroviral compound; an antiretroviral oral formulation to inhibit viral replication in HIV infected patients comprising efficient amounts of two different cytidine analogue reverse transcriptase inhibitors of different dosages in a pharmaceutically acceptable carrier to produce boosted cytidine analogue reverse transcriptase inhibitor antiretroviral compound in a patient cell; a method for the therapy of HIV infected patients comprising orally administrating the oral formulation.

(b) Description of Prior Art

An estimated 38.6 million people worldwide were living with HIV in 2005 according to the World Health Organization (WHO) (UNAIDS/WHO, 2006 Report on the Global AIDS epidemic. UNAIDS-Geneva, Switzerland, 2006.). Approximately 4.1 million persons acquired the human immunodeficiency virus (HIV) and 2.8 million individuals died in 2005 (UNAIDS/WHO, 2006.).

According to WHO, new simplified and less expensive approaches suitable for resource-poor settings are of greatest need.

Since the introduction of combination antiretroviral therapy, especially with the introduction of highly active antiretroviral therapy (HAART), HIV-related morbidity and mortality diminished significantly. However, in spite of progress and huge efforts, the HIV epidemic continues to expend (UNAIDS/WHO, 2006.). Moreover, HAART also led to the emergence, at an increasing rate, of adverse effects, metabolic abnormalities, body changes as well as drug resistance.

In order to offset these problems, new drugs, new drug combinations or approaches are continuously evaluated.

Antiretroviral regimens usually contain 2 nucleoside analogue reverse transcriptase inhibitors (NRTI) plus a protease inhibitor (PI) or a non-nucleoside reverse transcriptase inhibitor (NNRTI). Examples of NRTI are AZT (azidothymidine, zidovudine), d4T (stavudine), 3TC (lamivudine), ddC (zalcitabine), ddI (didanosine), abacavir (ziagen), FTC (emtricitabine). The approved NNRTI are: nevirapine, delavirdine, efavirenz. Among the protease inhibitors are saquinavir, indinavir, ritonavir, nelfinavir, lopinavir, atazanavir, amprenavir and tipranavir.

One of the most extensively utilized antiretroviral drugs being the backbone of most regimens is 3TC (2' deoxy-3'-thiacytidine or lamivudine). In addition to its excellent safety profile, this drug has beneficial virologic effects even in the presence of a mutation at the position 184 (M184V) of HIV reverse transcriptase conferring high-level resistance to 3TC (Diallo K, Götte M, and Wainberg M A. Molecular impact of the M184V mutation in human immunodeficiency virus type 1 reverse transcriptase. Antimicrob Agents Chemother 2003, 47: 3377-3383). This beneficial antiretroviral activity could be augmented by increasing the intracellular concentration of 3TC active form.

As for other NRTIs, 3TC requires intracellular metabolism to its active form 5'-triphosphate (3TC-TP) as seen in FIG. 2. This will compete with the natural endogenous nucleoside for the incorporation into nascent proviral DNA and will lead to DNA chain termination and consequently inhibition of HIV replication. The antiretroviral activity of 3TC (as that of the other NRTIs) is directly correlated with the intracellular 3TC-TP concentration. Both extracellular and intracellular factors affect this activation (phosphorylation to triphosphate). In vitro studies showed that, at an extracellular concentration of 10 μM of 3TC, there is clear evidence of saturation of 3TC-TP formation; in other words higher extracellular 3TC concentrations which may be obtained with higher 3TC doses do not necessarily increase the level of the active intracellular form, the 3TC-TP (Gray N M, Marr C L P, Penn C R, Cameron J M, and Bethell R C. The intracellular phosphorylation of (2', 3')-2-deoxy-3'-thiacytidine (3TC) and the incorporation of 3TC 5'-monophosphate into DNA by HIV-1 reverse transcriptase and human DNA polymerase γ. Biochem Pharmacol 1995, 50: 1043-1051). This fact was also confirmed in clinical studies in which an increased dose of 3TC (300 mg instead of 150 mg) did not significantly increased the 3TC-TP levels and did not result in a better clinical, virologic or immunologic effect (Eron J J, Benoit S L, Jemsek J, et al. Treatment with lamivudine, zidovudine, or both in HIV-positive patients with 200 to 500 CD4+ cells per cubic millimeter. N Engl J Med 1995, 333: 1661-1669.).

As the activation pathways for 3TC and of another NRTI, ddC (2'-3'-dideoxycytidine), are similar (as seen in FIG. 2), it is conceivable that concomitant administration of these drugs will influence each other's activation.

Initial in vitro data (with huge, non-physiologic doses of ddC) showed a negative interaction between 3TC and ddC (Veal G J, Hoggard P G, Barry M G, Khoo S, Back D J. Interaction between lamivudine (3TC) and other nucleoside analogues for intracellular phosphorylation. AIDS 1996, 10: 546-548). Therefore, the concurrent use of ddC (daily doses of 2.25 mg) and 3TC are currently contraindicated because of their reciprocal inhibition of activities (ddC competes with the 3TC's activation and vice versa).

In conclusion, so far, no valid approach to increase intracellular 3TC-TP and, hence, its antiretroviral activity, was reported. It is imperative and timely to find a new therapeutic approach able to increase intracellular levels of 3TC-TP without increasing the drug-related toxicities, especially in patients harboring an HIV strain with reduced 3TC susceptibility or with a suboptimal control of HIV infection.

SUMMARY OF THE INVENTION

The present invention is based on the findings that a low dose of a cytidine derivative such as ddC is capable of boosting the activity of 3TC. Our approach allows improvement of the 3TC antiretroviral activity by increasing the intracellular active form of 3TC, namely the 3TC-TP. This effect is obtained by using a reduced dose of ddC for its <<booster>> effect in combination with the usual dose of 3TC. With the reduced daily dosage, the ddC concentrations in blood and tissues are minimal and therefore, no additional significant toxicity is encountered or expected. It represents an additional therapeutic option in combination with other antiretrovirals, and it is valuable especially in cases of HIV infection with reduced 3TC susceptibility or suboptimal virologic control. In addition, the use of this therapeutic approach will enable a larger number of people to benefit from the inclusion of 3TC (with a heighten antiretroviral potency) in their therapeutic regimens.

The new antiretroviral formulation comprises 3TC and a "boosting" dose of a cytidine derivative such as ddC administered once or twice daily, alone or in conjunction with other antiretrovirals such as a NRTI (e.g. abacavir), a protease inhibitor or a NNRTI. This new cytidine derivatives combination could be formulated in one tablet or capsule. Like ddC, other cytidine derivatives (namely FTC or emtricitabine, DPC 817 and others) could also be used at different reduced dosages in combination with 3TC, because they share the same intracellular activation pathways, and should be considered as ddC <<equivalents>>. On the other hand, low dose ddC might also increase intracellular concentrations of active forms of other cytidine compounds, such as emtricitabine, as it does for 3TC.

In accordance with the present invention, there is provided an oral formulation to inhibit viral replication in HIV infected patient which comprises efficient amounts of a first and a second cytidine analogue reverse transcriptase inhibitors in different dosages in association with a pharmaceutically acceptable carrier and further comprising a least one other antiretroviral to produce boosted cytidine analogue reverse transcriptase inhibitor antiretroviral compound, wherein the boosted molecule is a first cytidine analogue which antiretroviral activity is boosted by an interaction with a second cytidine analogue in a patient cell and wherein the first and second cytidine analogues are different.

In accordance with the present invention, there is provided an intracellular boosted cytidine analogue reverse transcriptase inhibitor antiretroviral compound consisting of a first intracellular cytidine analogue reverse transcriptase inhibitor molecule which antiretroviral activity is boosted by an interaction with a second cytidine analogue in a patient's cells, wherein the second analogue is at a lower dosage than the first analogue thereby increasing the antiretroviral activity of the first analogue and wherein the first and second cytidine analogues are different.

The first and second cytidine analogue reverse transcriptase inhibitors are different molecules chosen from 3TC (lamivudine), ddC (zalcitabine), FTC, emtricitabine, DPC817 and from other derivatives of cytidine, deoxycytidine, fluorocytidine and their negative enantiomers.

The formulation may further comprise another antiretroviral, which may be chosen from a nucleoside reverse transcriptase inhibitor (NRTI), a non-nucleoside reverse transcriptase inhibitor (NNRTI) and a protease inhibitor.

In accordance with a preferred embodiment of the present invention, the dose of the first citydine derivative, when it is 3TC, may vary from 150 mg to 300 mg.

In accordance with another preferred embodiment of the present invention, the dose of the second cytidine derivative, when it is ddC, may vary from 0.375 mg to 0.75 mg.

In accordance with a preferred embodiment of the present invention, the pharmaceutically acceptable carrier's form is chosen from a tablet, a capsule, a jellified tablet, a caplet and a liquid formulation.

In accordance with the present invention, there is provided a method for the therapy of HIV infected patients for decreasing or maintaining the viral load below the limit of detection, which comprises orally administering the oral formulation of the present invention.

In accordance with another embodiment of the method of the present invention, the formulation may be administered once or twice daily.

In accordance with still another embodiment of the method of the present invention, the patients are HIV infected patients comprising patients harboring an HIV strain with 3TC reduced susceptibility, patients with suboptimal virologic control or those with limited resources.

For the purpose of the present invention the following terms are defined below.

The expression "patients harboring an HIV strain with reduced 3TC susceptibility" refers to patients infected with an HIV strain presenting a mutation at position 184 (M184V) of its reverse transcriptase, therefore conferring high level drug resistance, especially to 3TC.

The expression "patients with suboptimal virologic control" refers to patients who, in spite of a triple or quadruple therapy, still have a detectable HIV viral load (the amount of HIV in the blood); optimal control refers to an HIV viral load below the detection limit (less than 50 HIV-1 RNA copies/ml).

The expression "patients with limited resources" is referring to the patients living in areas with poor resources or treated in poor resource settings. A harm-reduction approach is now considered a viable one as it was realized (WHO) that is impossible to offer a triple therapy to all HIV-infected people worldwide. 3TC alone was already evaluated and had potential benefits. An improved formulation as that we propose will increase the benefit of 3TC therapy.

DETAILED DESCRIPTION OF THE INVENTION

This invention will be described referring to specific embodiments and to the appended figures, the purpose of which is to illustrate the invention and not to limit the scope thereof.

Figure 2:
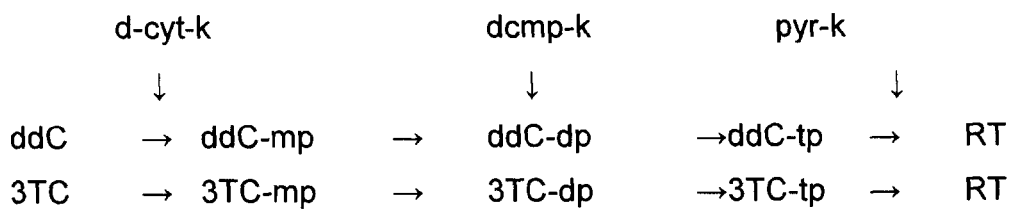
FIG. 2 illustrates a scheme, which establishes the various stages of the phosphorylation pathway of cytidine reverse transcriptase inhibitor analogues. The particular pathway of 3TC and ddC is detailed.

Boosted cytidine analogue reverse transcriptase inhibitor antiretroviral compound can be, in one embodiment of the present invention, "zalcitabine-boosted 3TC". Such particular compound consists of the combination of a "usual" dose of 3TC [150 mg-300 mg] with a reduced dose of ddC given twice or even once daily. In this way the total ddC daily dose is only ⅓ to ⅙ of the routine dosage (<<a usual>> dose of 2.25 mg is reduced to 0.375 mg to 0.75 mg/day). Both 3TC and ddC are cytidine nucleoside analogues and they share the same phosphorylation (activation) pathway, which is depicted in FIG. 2. Other derivatives of cytidine, deoxycytidine, fluorocytidine or their negative enantiomers may have the same effects on the 3TC intracellular activation. Also, low dose ddC may have the same effects on intracellular concentration of other cytidine derivatives.

The product is used alone or in combination with another antiretroviral and administered as an oral formulation. Antiretroviral oral formulation is in the form of a tablet, a capsule, a jellified tablet, a caplet and as a liquid formulation. The oral formulation is administered as a therapy for HIV-infected patients, harboring an HIV strain with reduced susceptibility, patients having a suboptimal virologic control (viral load detectable) and finally as a single therapy in resource-poor settings.

The present invention will be more readily understood by referring to the following examples, which are given to illustrate the invention rather than to limit its scope.

EXAMPLE I

Zalcitabine in a daily dosage of up to 0.75 mg was used in combination with 3TC and another antiretroviral for the treatment of HIV infection. The reason to combine the reduced dose ddC with 3TC was to increase the active form and, consequently, the antiretroviral activity, of 3TC. This combination was named <<zalcitabine-boosted>> 3TC.

<<Zalcitabine-boosted 3TC>> in combination with indinavir optimally controlled the HIV infection in a patient with an AIDS-defining infection (toxoplasmosis). When abacavir (an NRTI) was substituted for indinavir (a protease inhibitor) this effect continued to be optimal (HIV viral load below the level of detection, i.e. <50 HIV-1 RNA copies/ml). Moreover this effect is sustained in time for more than 7 years. If we consider the zalcitabine-boosted 3TC as a single drug (the effect being due to 3TC quasi-exclusively), its combination with abacavir represents only a dual not a triple therapy. This effect was not described in patients with advanced HIV infection. In addition, this regimen (zalcitabine-boosted 3TC) is convenient to administer being given only twice or even once daily.

Non-boosted 3TC in combination with full-dose ddC and AZT (zidovudine) was equivalent to dual 3TC plus AZT therapy in other patients.

EXAMPLE II

The use of 3TC in combination with ddC was formally contraindicated since 1996 when it was shown that 3TC inhibited ddC phosphorylation in a concentration-dependent manner at identical concentration ratios of 10 to 100 µM (Veal G J, Hoggard P G, Barry M G, Khoo S, Back D J. Interaction between lamivudine (3TC) and other nucleoside analogues for intracellular phosphorylation. AIDS 1996, 10: 546-548). This level of inhibition was much greater compared to the effect of ddC on 3TC phosphorylation. While ddC did inhibit in vitro 3TC phosphorylation, this occurred at extremely high concentrations of ddC (10 to 100 higher than those of 3TC) (Veal G J et al., 1996; Kewn S, Veal G J, Hoggard P G, Barry M G, Back D J. Lamivudine (3TC) phosphorylation and drug interactions in vitro. Biochem Pharmacol 1997, 54: 589-595). This is unlikely to occur in clinical practice, because the 3TC plasma levels are much higher than those of ddC (e.g. 5 µM vs. 0.5-1.5 µM).

The in vivo toxicity index of ddC (the ratio between the toxic concentration to the concentration needed for antiretroviral activity) is very low: 0.2 µM/0.1 µM. It is therefore obvious that reduced dosages of ddC will certainly reduce its toxicity. So far we did not note signs or symptoms of ddC toxicity with ddC-boosted 3TC.

Although, this drug combination is contraindicated by all guidelines for the use of antiretrovirals in HIV infection and by studies on pharmacokinetics and drug-drug interactions, our results suggest that this is not the case with the approach and the formulation we use (lower doses of ddC combined to 3TC).

<<Zalcitabine-boosted 3TC>> has an important and sustained antiretroviral activity, enabling an optimal virologic control when used in combination with other NRTI or a protease inhibitor. When the antiretroviral activity of 3TC in combination with ddC was tested in vitro (results published in 2000) the combination had a slightly better activity in comparison with each drug used alone (Hoggard P G, sales S D, Kewn S, et al. Correlation between intracellular pharmacological activation of nucleoside analogues and HIV suppression in vitro. Antivir Chem Chemother 2000, 11: 353-358). However, the antiretroviral activity of 3TC plus ddC, as measured by the effect on p24 production in vitro, was inferior to that of 3TC plus AZT. The authors did not recommend the combination of 3TC with ddC for clinical practice (Hoggard P G et al., 2000).

Without being bound to any theory, we believe that the boosting effect of ddC on 3TC activation is due to higher intracellular levels of 3TC-triphosphate that could overcome the concentrations necessary for the inhibition of HIV strains with reduced susceptibility or resistant to 3TC. Also, these higher intracellular concentrations will extend the 3TC antiretroviral activity in viral <<sanctuaries>> such as the nervous system, eyes, genitalia and also other organs, tissues, or cells in which 3TC do not achieve optimal antiretroviral levels with the usual therapeutic regimens. This was proven by measuring the 3TC triphosphate levels in peripheral blood mononuclear cells.

We first proceeded to the evaluation of plasmatic 3TC levels to determinate the effect of ddC on this compound, prior to its intracellular incorporation and phosphorylation. The results were compiled in Table 1.

TABLE 1

Plasmatic 3TC levels for patients with or without ddC-boosted 3TC treatment.

| Patient no. | Date | 3TC plasma levels Pre-dose (ng/ml) | 2 h post dose (ng/ml) | Comment |
| --- | --- | --- | --- | --- |
| DC001 | 29 Sep. 2003 | 423 | 1145 | 1st patient |
| JMC002 | 26 Oct. 2004 | 193 | 1078 | |
| MMP003 | 28 Oct. 2004 | 326 | 620 | |
| BSB 004 | 25 Nov. 2004 | 143 | 700 | Without ddC |
| BSB | 02 Dec. 2004 | 308 | 1500 | After 7 days of ddC-boosted 3TC |
| AD005 | 13 Sep. 2004 | 35 | 779 | Without ddC |
| AD005 | 20 Sep. 2004 | 37 | 510 | After 7 days of ddC-boosted 3TC |
| PP006 | 13 Sep. 2004 | 35 | 1057 | Without ddC |
| PP006 | 20 Sep. 2004 | 229 | 1210 | After 7 days of ddC-boosted 3TC |

As seen in Table 1, patients who were already on ddC-boosted 3TC when the dosage was performed had good pre and post dosage concentrations. Among the 3 patients who had dosages performed with and without ddC as a booster, 2 of them had increased levels whereas one (AD005, who had chronic diarrhea) had no effect of ddC-boosted 3TC. It should be noted that for the plasma levels, the peak (post-dose) was at about 2 hours of the drug administration: this is not the case with intracellular triphosphate concentrations where the peaks might occur later than 2 hours post drug administration.

With a highly sensitive technique (Becher F, Pruvost A, Goujard C, et al. Improved method for the simultaneous determination of d4T, 3TC and ddI intracellular phosphorylated anabolites in human peripheral-blood mononuclear cells using high-performance liquid chromatography/tandem mass spectrometry. Rapid Commun Mass Spectrom 2002, 16: 555-565), we also measured the intracellular 3TC triphosphate (3TC-TP) levels in 6 patients while taking 3TC and ddC. In three of them the 3TC-TP levels have been measured while the patients were not yet receiving ddC as well as 7 days after added low dose ddC.

Data in the literature report 3TC-TP levels of about 1-5 μmol/10⁶ PBMC. However, at the laboratory were the tests have been performed (and with their method) the average intracellular 3TC-TP levels in HIV-treated patients are around 5 and up to 15 μmol/10⁶ cells.

The 3TC-TP levels have been measured both before administering a new dose (the nadir or the lowest level) and 2 hours after the dose (peak level). This time interval (2 hours) for the peak level was chosen taking into account the values for plasma levels because the time to peak intracellular levels is not well documented. It is also more convenient for the patient. However, the time to nadir and especially the time to peak intracellular levels could be longer than that and therefore it is better to report the concentrations before a given dose and 2 hours later on. The results (in pmol/10⁶ cells) are presented in FIG. 1 and Table 2.

TABLE 2

Intracellular 3TC-TP levels: total amount (in pmol)/10⁶ cells

| Patient no. | Pre-dose | 2 h post dose | Comment |
|---|---|---|---|
| DC001 | 13.4 | 20.9 | The initial patient |
| JMC002 | 22.0 | 22.6 | Time to peak could be longer than 2 hours.* |
| MMP003 | 24.7 | 22.7 | Time to peak could be much longer than 2 hours; probably at 2 hours post dose we have the nadir and the peak might be at >4 hours after dose. |
| BSB004 | 21.9 | 17.4 | Time to peak could be much longer than 2 hours; probably at 2 hours post dose we have the nadir and the peak might be at >4 hours after dose. |
| AD005 | 19.9 | 28.2 | |
| PP006 | 25.9 | 43.9 | |

Figure 1:
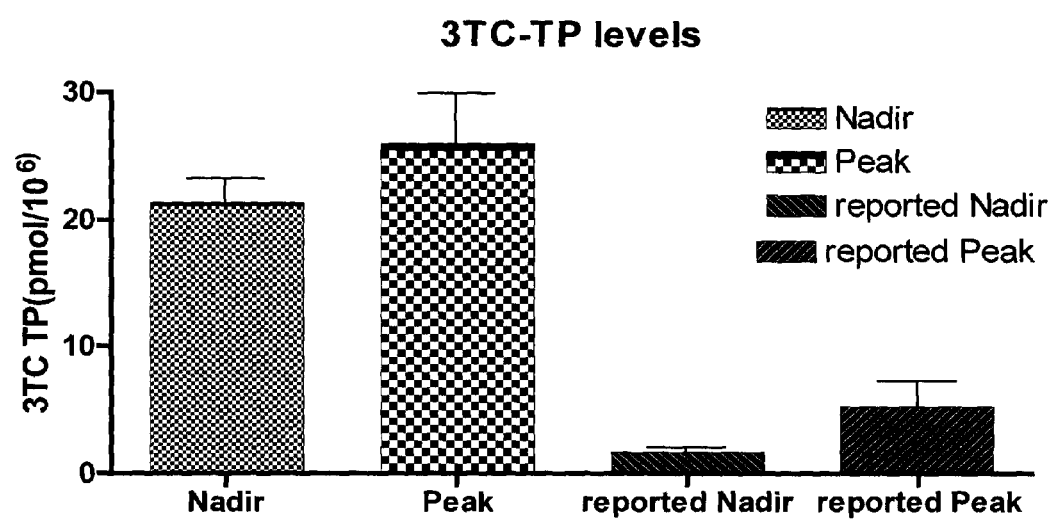
FIG. 1 illustrates the intracellular levels of 3TC-TP at their lowest value (Nadir) and at their highest value fixed at 2 hours after administration when co-administered with ddC and compared with the intracellular 3TC-TP published in the literature.

As can be seen from Table 2 and FIG. 1, the 3TC-TP intracellular levels in patients taking ddC-boosted 3TC are much elevated than those reported in the literature in patients taking 3TC-containing antiretroviral therapy without added ddC. The fact that 2 hours after the dose the levels did not increased in 2 out of 6 patients may reflect the longer time to peak intracellular levels than the time to peak plasma levels which is usually 2 hours. In addition in one of them (BSB004) the PBMC count was much higher 2 hours after the dose. This may have also individual variations.

In three of the above patients we measured the intracellular 3TC-TP levels at 2 time points: during 3TC-containing treatment regimens and 7 days after adding low dose ddC. They are presented in Table 3 below.

TABLE 3

Intracellular 3TC-TP levels: total amount (in pmol/10⁶) while on 3TC without ddC and 7 days after adding ddC to 3TC-containing antiretroviral therapy.

| Patient no. | Pre-dose | 2 h post dose | Comment |
|---|---|---|---|
| BSB004 + ddC | 21.9 | *17.4* | Time to peak could be much longer than 2 hours; probably at 2 hours post dose we have the nadir and the peak might be at >4 hours after dose. |
| no ddC | 18.8 | 21.1 | |
| AD005 + ddC | *19.9* | 28.2 | Had very high levels of 3TC-TP before adding ddC. So ddC did not increased further the 3TC-TP levels |
| no ddC | 36 | 26.2 | |
| PP006 + ddC | 25.9 | 43.9 | |
| no ddC | 17.5 | 22.2 | |

In Table 3, for 4 out of 6 patient determinations, the 3TC-TP levels were higher after adding ddC. The no increase in 3TC-TP levels in the other 2 instances (in italics) were noted once before the dose (at nadir) in patient ADD005 and once post-dose (at peak) in patient BSB004 both of them having already very high 3TC-TP levels in absence of ddC.

These 3TC-TP levels we found are much higher than $IC_{50}$ (Inhibitory concentration for 50% of virions) for susceptible strains and even for moderately susceptible and low level resistant strains. In addition these elevated levels may indicate that therapeutic concentrations are reached in HIV reservoirs of slowly multiplying or "dormant" mononuclear cells.

In other 3 patients with suboptimal virologic control, (see Table 4. Immunological and Virologic data) ddC-boosted 3TC decreased the HIV viral load. Indeed, adding ddC-boosted 3TC to the failing therapeutic regimen significantly decreased the viral load (optimizing therapy).

TABLE 4

Immunological and Virologic data

| Patient no. | Date | CD4+ | Viral load | Comment |
|---|---|---|---|---|
| DC001 | | Started ddC-boosted 3TC in 1998 | | The initial patient had AIDS |
| | 29 Apr. 2002 | 640 | 1 225 | Viral rebound after stopping antiretrovirals for a month; restarted after this visit |
| | 24 Sep. 2002 | 550 | <50 | |
| | 28 May 2003 | 580 | <50 | |
| | 29 Sep. 2003 | 650 | <50 | Dosage 3TC |
| MMP003 | 28 Sep. 2004 | 180 | 291 392 | ddC started after 1$^{st}$ dosage |
| | 28 Oct. 2004 | 220 | 8 510 | 2$^{nd}$ dosage (after 7 days of ddC-boosted 3TC) |

TABLE 4-continued

Immunological and Virologic data

| Patient no. | Date | CD4+ | Viral load | Comment |
|---|---|---|---|---|
| BSB004 | 25 Nov. 2004 | 760 | 1 344 | ddC started after $1^{st}$ dosage |
| | 02 Dec. 2004 | 540 | 1 113 | $2^{nd}$ dosage (after 7 days of ddC-boosted 3TC) |
| | 25 Jan. 2005 | 730 | 378 | |
| CC | 01 Nov. 2005 | 220 | 124 | ddC started 11 Nov. 2005 |
| | 29 Dec. 2005 | 290 | <50 | |
| DF | 20 Apr. 2005 | 770 | 445 | ddC started after $1^{st}$ dosage. |
| | 27 Apr. 2005 | 960 | 453 | $2^{nd}$ dosage (after 3 days of ddC-boosted 3TC) |
| | 30 Aug. 2005 | 660 | 97 | |

We therefore contemplate that any other cytidine derivative which shares the same pathway of activation as 3TC will be equivalent to ddC in the present combination. Moreover, other cytidine derivatives intracellular levels may be increased by low dose ddC, as it is the case with 3TC.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. An oral formulation consisting essentially of 2',3'-dideoxy-3'-thiacytidine (3TC), 2'-3'-dideoxycytidine (ddC), and a pharmaceutically acceptable carrier, wherein said ddC is at a dosage varying from 0.375 mg to 0.750 mg, and wherein said oral formulation is an once daily oral formulation.

2. The oral formulation according to claim 1, wherein said 3TC is at a dosage varying from 150 mg to 300 mg.

3. The oral formulation according to claim 2, wherein said formulation is effective to inhibit viral replication in HIV infected patients.

4. The oral formulation according to claim 1, wherein said oral formulation is in the form of a tablet, a capsule, a jellified tablet, a caplet or a liquid formulation.

5. The oral formulation of claim 2, wherein said formulation is effective for decreasing and maintaining viral load below the limit of detection in HIV infected patients.

* * * * *